United States Patent [19]

Murase et al.

[11] Patent Number: 5,503,776

[45] Date of Patent: Apr. 2, 1996

[54] N-ACYLCARNOSINES AND THEIR USE AS ANTIOXIDANTS

[75] Inventors: Hironobu Murase, Gifu; Tsutomu Kunieda, Ibi, both of Japan; Akihiko Nagao, Iowa; Junji Terao, Tsukuba, Japan

[73] Assignees: National Food Research Institute Ministry of Agriculture, Forestry and Fisheries, Ibaraki; CCI Corporation, Gifu, both of Japan

[21] Appl. No.: 361,446

[22] Filed: Dec. 21, 1994

Related U.S. Application Data

[62] Division of Ser. No. 837,078, Feb. 18, 1992, abandoned.

[30] Foreign Application Priority Data

Feb. 19, 1991 [JP] Japan ..................... 3-024655

[51] Int. Cl.$^6$ .................. C07D 237/22; B01F 17/28; C07C 231/10; C07K 1/02; C07K 5/06; C07K 5/08; C09K 15/22; C09K 3/00
[52] U.S. Cl. .................. 252/397; 252/401; 252/403; 252/405; 548/312.7; 548/313.4; 548/313.7; 548/326.5; 548/331.1; 548/331.5; 548/332.1; 548/332.5; 548/333.5; 548/334.1; 548/334.5; 548/335.1; 548/335.5; 548/338.1; 548/340.1; 548/341.1; 548/341.5; 554/36; 554/37; 560/16; 560/39; 560/40; 560/41; 560/153; 560/169; 562/426; 562/444; 562/445; 562/448; 562/450
[58] Field of Search .................. 554/36, 37; 560/153, 560/169, 16, 39, 40, 41; 562/426, 444, 445, 448, 450; 548/312.7, 313.4, 313.7, 326.5, 331.1, 331.5, 332.1, 332.5, 333.5, 334.1, 334.5, 335.1, 335.5, 338.1, 340.1, 341.1, 341.5; 252/397, 401, 403, 405

[56] References Cited

FOREIGN PATENT DOCUMENTS

| | | |
|---|---|---|
| 0139481 | 5/1985 | European Pat. Off. . |
| 57-64677 | 4/1982 | Japan .................. 548/338.1 |
| 57-165371 | 10/1982 | Japan .................. 548/338.1 |
| 58-124750 | 7/1983 | Japan .................. 548/338.1 |
| 58-135868 | 8/1983 | Japan .................. 548/338.1 |
| 58-188862 | 11/1983 | Japan .................. 548/338.1 |
| 5-65275 | 3/1993 | Japan .................. 548/338.1 |
| 1354622 | 5/1974 | United Kingdom ........ 548/338.1 |
| 9014429 | 11/1990 | WIPO . |

OTHER PUBLICATIONS

J. Lipid. Research 8, 142 (1967) pp. 142–145.
Chem. Abstr., Registry Handbook; 1987 Supplement Reg. No. 107768–12–7.
Chem. Abstr. vol. 82, No. 160570g (1975).

*Primary Examiner*—Floyd D. Higel
*Attorney, Agent, or Firm*—The Firm of Gordon W. Hueschen

[57] ABSTRACT

An N-acylamino acid compound represented by the general formula (1):

$$R\text{—}CO\text{—}(NH\text{—}X\text{—}CO)_n\text{—}OR^1 \qquad (1)$$

wherein (NH—X—CO) is an amino acid residue, X in (NX—X—CO) is variable with the kind of amino acid to be used, R—CO is a saturated or an unsaturated fatty acid residue having 6 to 24 carbon atoms, $R^1$ is hydrogen atom, sodium atom, potassium atom, or methyl group and n is an integer in the range of from 1 to 3, indicating that at least one histidine is contained as a component amino acid is disclosed, which is obtained by causing an N-hydroxysuccinimide ester to react with an amino acid or a peptide.

The compound excels in antioxidizing power, emulsifying power, antibacterial power, chelating power, infrared absorbing power, and humidity-retaining power.

8 Claims, 8 Drawing Sheets

N-ACYLCARNOSINES AND THEIR USE AS ANTIOXIDANTS

The application is a division of our prior-filed application Ser. No. 07/837,078 filed Feb. 18, 1992, now abandoned.

BACKGROUND OF THE INVENTION

1. Field of the Invention

This invention relates to novel N-acylamino acid compounds and a method for the production thereof. More particularly, it relates to novel compounds produced by acylating histidine and peptide containing histidine with a long-chain fatty acid and possessed of many functionalities such as antioxidizing power, emulsifying power, antibacterial power, chelating power, ultraviolet absorbing power, and humidity-retaining power and a method for the production thereof.

2. Description of the Prior Art

In recent years, the postulate that active oxygen induces various oxidizing reactions and constitutes itself a notorious cause for various diseases such as senility, arteriosclerosis, and cancers has come to be advocated and studies devoted to the development of an antioxidant capable of inhibiting the oxidzing reactions have been gaining in impetus. In the food industry, for example, such synthetic antioxidants as BHT (3,5-t-butyl-4-hydroxy toluene) and BHA (2,(3)-6-butyl-4-hydroxy anisole) are used as inexpensive and highly efficient antioxidants.

Since the detection of the carcinogenic action in these compounds, particularly in BHA, was reported, doubts have come to be cast on the safety of the compounds. Tocopherols which are used as naturally occurring antioxidants, in spite of their outstanding antioxidizing power, betray sparing solubility in water and liability to promote oxidation at a high concentration and, therefore, find only restricted utility in cosmetic preparations and foodstuffs. Other polyphenols which are possessed of an antioxidizing power fit only restricted applications on account of their weak point of exhibiting high solubility in water and sparing solubility in oil.

An object of this invention, therefore, is to provide novel acyl compounds and a method for the production thereof.

Another object of this invention is to provide novel compounds possessed of functionalities such as antioxidizing power, emulsifying power, antibacterial power, chelating power, ultraviolet absorbing power, and humidity-retaining power and a method for the production thereof.

These objects are accomplished by an N-acylamino acid compound represented by the general formula (1):

wherein (NH—X—CO) is an amino acid residue, X in (NH—X—CO) is variable with the kind of an amino acid to be used, R—CO is a saturated or unsaturated fatty acid residue having 6 to 24 carbon atoms, $R^1$ is hydrogen atom, sodium atom, potassium atom, or methyl group, and n is an integer in the range of from 1 to 3, indicating that at least one histidine is contained as a component amino acid.

These objects are further accomplished by a method for the production of an N-acylamino acid compound represented by the general formula (1):

wherein (NH—X—CO) is an amino acid residue, X in (NH—X—CO) is variable with the kind of an amino acid to be used, R—CO is a saturated or unsaturated fatty acid residue having 6 to 24 carbon atoms, $R^1$ is hydrogen atom, sodium atom, potassium atom, or methyl group, and n is an integer in the range of from 1 to 3, indicating that at least one histidine is contained as a component amino acid, characterized by causing an N-hydroxysuccinimide ester represented by the general formula (2):

wherein R—CO has the same meaning as defined above, to react with an amino acid or a peptide represented by the general formula (3):

wherein (NH—X—CO), X, R—CO, $R^1$, and n have the same meanings as defined above, indicating that at least one histidine is contained as a component amino acid.

The objects are also accomplished by an antioxidant having as an active component thereof an N-acylamino acid compound represented by the general formula (1):

wherein (NH—X—CO) is an amino acid residue, X in (NH—X—CO) is variable with the kind of an amino acid to be used, R—CO is a saturated or unsaturated fatty acid residue having 6 to 24 carbon atoms, $R^1$ is hydrogen atom, sodium atom, potassium atom, or methyl group, and n is an integer in the range of from 1 to 3, indicating that at least one histidine is contained as a component amino acid.

The objects are further accomplished by an emulsifier having as an active component thereof an N-acylamino acid compound represented by the general formula (1):

wherein (NH—X—CO) is an amino acid residue, X in (NH—X—CO) is variable with the kind of an amino acid to be used, R—CO stands for a saturated or unsaturated fatty acid residue having 6 to 24 carbon atoms, $R^1$ is hydrogen atom, sodium atom, potassium atom, or methyl group, and n is an integer in the range of from 1 to 3, indicating that at least one histidine is contained as a component amino acid.

The N-acylamino acid compounds and the method for production thereof according to this invention are as described above and, therefore, are novel to the art. These compounds are novel antioxidants which exhibit an antioxidizing power in polar and nonpolar solvents. Further, these compounds are possessed of a very high emulsifying power and antibacterial power, chelating power, ultraviolet absorbing power, and warmth-retaining power as well and, therefore, are highly useful as raw materials for cosmetic goods, foodstuffs, medicines, etc.

EXPLANATION OF THE PREFERRED EMBODIMENT

The N-acylamino acids, N-acylpeptide compounds, salts thereof and methyl ester thereof which are contemplated by this invention (hereinafter referred to collectively as "N-acylamino acid compounds") are the compounds which are represented by the general formula (1), wherein R—CO is a saturated or unsaturated fatty acid residue having 6 to 24, preferably 8 to 20, carbon atoms. The fatty acid residues which answer this description include capryloyl ($C_8$), caprinoyl ($C_{10}$), lauroyl ($C_{12}$), myristoyl ($C_{14}$), palmitoyl ($C_{16}$), oleoyl ($C_{18:1}$), linoleoyl ($C_{18:2}$), linolenoyl ($C_{18:3}$), stearoyl ($C_{18}$), and arachidoyl ($C_{20}$), for example.

The part (NH—X—CO) of the general formula is an amino acid residue and the symbol X found in this part is variable with the kind of an amino acid to be used. The amino acids which are usable herein include histidine (His), glycine (Gly), tryptophan (Trp), isoleucine (Ile), phenylalanine (Phe), methionine (Met), cysteine (Cys), leucine (Leu), lysine (Lys), alanine, valine, proline, serine, threonine, tyrosine, asparagine, glutamine, arginine, aspartic acid, glutamic acid, beta-alanine, dopa, creatine, and ornithine (in the case of the amino acids having both D and L forms, they are usable in both forms), for example. Branched peptides are usable when they fulfil the aforementioned condition. (Of the amino acids cited above, those which are appended by a parenthesized abbreviation will be referred to hereinbelow by the relevant abbreviations.)

Then, n is an integer of 1 to 3, preferably 1 or 2, indicating that at least one His is contained as a component amino acid. The amino acid residue of (NH—X—CO), therefore, is a His residue when n is 1 or a peptide reissue when n is 2 or 3. When n is 2, the amino acid residues which are available herein include -His-His, -Gly-His, -His-Gly, -His-Leu, -Leu-His, -Trp-His, -His-Trp, -Ile-His, -His-Ile, -Phe-His, -His-Phe, -Met-His, -His-Met, -Cys-His, -His-Cys, beta-3-methyl-L-His, gamma-aminobutylyl-L-His, and carnosine (beta-alanyl-L-His), for example. When n is 3, the amino acid residues available herein include -His-His-His, -Gly-His-Lys, -Gly-His-His, -Gly-Gly-His, -Ile-His-His, -Ile-Ile-His, -Phe-His-His, -Phe-Phe-His, -Met-His-His, -Met-Met-His, -Cys-His-His, -Cys-Cys-His, -Trp-His-His, and -Trp-Trp-His, for example.

The N-acylamino acid compounds of this invention are the compounds which contain the aforementioned fatty acid residues and amino acid residues as component elements, salts thereof, and methyl ester of the compounds. They particularly include N-capryroyl-His, N-capryroyl-His-His, N-capryroyl-His-Leu, N-capryroyl-Leu-His, N-capryroyl-beta-alanyl-3-methyl-L-His, N-capryroyl-gamma-aminobutylyl-L-His, N-capryroyl-carnosine, N-capryroyl-His-His-His, N-capryroyl-Gly-His-Lys, N-capryroyl-Gly-His-His, N-capryroyl-Gly-Gly-His, N-caprinoyl-His, N-caprinoyl-His-His, N-caprinoyl-His-Leu, N-caprinoyl-Leu-His, N-caprinoyl-beta-alanyl-3-methyl-L-His, N-caprinoyl-gamma-aminobutylyl-L-His, N-caprinoyl-carnosine, N-caprinoyl-His-His-His, N-caprinoyl-Gly-His-Lys, N-caprinoyl-Gly-His-His, N-caprinoyl-Gly-Gly-His, N-lauroyl-His, N-lauroyl-His-His, N-lauroyl-His-Leu, N-lauroyl-Leu-His, N-lauroyl-beta-alanyl-3-methyl-L-His, N-lauroyl-gamma-aminobutylyl-L-His, N-lauroyl-carnosine, N-lauroyl-His-His-His, N-lauroyl-Gly-His-Lys, N-lauroyl-Gly-His-His, N-lauroyl-Gly-Gly-His, N-myristoyl-His, N-myristoyl-carnosine, N-palmitoyl-His, N-palmitoyl-His-His, N-palmitoyl-His-Leu, N-palmitoyl-Leu-His, N-palmitoyl-beta-alanyl-3-methyl-L-His, N-palmitoyl-gamma-aminobutylyl-L-His, N-palmitoyl-carnosine, N-palmitoyl-His-His-His, N-palmitoyl-Gly-His-Lys, N-palmitoyl-Gly-His-His, N-palmitoyl-Gly-Gly-His, N-oleoyl-His, N-oleoyl-His-His, N-oleoyl-His-Leu, N-oleoyl-Leu-His, N-oleoyl-beta-alanyl-3-methyl-L-His, N-oleoyl-gamma-aminobutylyl-L-His, N-oleoyl-carnosine, N-oleoyl-His-His-His, N-oleoyl-Gly-His-Lys, N-oleoyl-Gly-His-His, N-oleoyl-Gly-Gly-His, N-linoleyl-His, N-linoleyl-carnosine, N-linolenyl-His, N-linolenyl-carnosine, N-stearoyl-His, N-stearoyl-His-His, N-stearoyl-His-Leu, N-stearoyl-Leu-His, N-stearoyl-beta-alanyl-3-methyl-L-His, N-stearoyl-gamma-aminobutylyl-L-His, N-stearoyl-carnosine, N-stearoyl-His-His-His, N-stearoyl-Gly-His-Lys, N-stearoyl-Gly-His-His, N-stearoyl-Gly-Gly-His, N-arachidoyl-His, and N-arachidoyl-carnosine, for example.

The N-acylamino acid compound of this invention is obtained by causing an N-hydroxysuccinimide ester represented by the general formula (2) to react with an amino acid or a peptide represented by the general formula (3) as described above.

This N-hydroxysuccinimide ester is obtained by causing a saturated or unsaturated fatty acid having 6 to 24 carbon atoms to react with an N-hydroxysuccinimide in an organic solvent such as, for example, ethyl acetate in the presence of a dichlorohexyl carbodiimide.

The N-acylamino acid compound is obtained easily in a high yield by causing this N-hydroxysuccinimide ester to react with an amino acid or a peptide in an organic solvent such as, for example, tetrahydrofuran under an alkaline condition at normal room temperature. In this reaction, the amount of the amino acid or peptide to be used is desired to be in the range of from 0.1 to 5 mols, preferably from 0.5 to 2 mols, per mol of the N-hydroxysuccinimide ester.

The alkaline condition is in the range of from pH 7 to pH 12, preferably from pH 8 to pH 11. The adjustment of this alkaline condition is obtained by the use of sodium carbonate, potassium carbonate, sodium hydrogen carbonate, or potassium hydrogen carbonate, for example.

The N-acyl-His and N-acyl-His-containing peptides (particularly N-acyl-carnosine (carnosine: beta-alanyl-L-His, which occurs in a high concentration in the brain and the muscles of man)) which are obtained as described above are amphipatic substances and are possessed of the following functionalities. For example, they are capable of repressing the speed of peroxidation of a higher fatty methyl ester in a nonaqueous hexane-isopropyl alcohol solution. When a liposome is formed of vital membrane as a model with egg yolk lecithin in an aqueous system and the oxidation reaction of the liposome is promoted with ferrous-ascorbate system, the N-acyl compound incorporated in the liposome in advance is capable of repressing the speed of this oxidation. Thus, it has been confirmed that the N-acyl-His and N-acyl-His-containing peptides (particularly N-acyl-carnosine) are possessed of the power of chelating an iron ion in addition to the antioxidizing power for curbing the formation of a peroxide. When these compounds were tested for emulsifying power in an oil-water system, they were found to have stronger emulsifying power under fixed set of conditions than such commercially available emulsifiers as casein, sugar ester, and Triton X100. It is quite evident that these compounds are possessed of the power to absorb ultraviolet light because they have numerous double bonds on the amino acid residue side.

Now, this invention will be described below with reference to working examples. It should be noted, however, that the scope of this invention is not limited in any respect by these working examples.

Referential EXAMPLE 1

In 130 ml of ethyl acetate, 3.45 g (30 m.mols) of N-hydroxysuccinimide was dissolved and then 3.45 g (30 m.mols) of oleic acid was dissolved. The resultant solution and a solution of 6.18 g (30 m.mols) of dicyclohexyl carbodiimide in 10 ml of ethyl acetate added thereto were stirred at normal room temperature with a magnetic stirrer and thus left reacting with each other for 15 hours. From the resultant reaction solution, about 7 g of the N-hydroxysuccinimide ester of oleic acid of high purity was obtained by repeatedly subjecting the reaction solution to the treatment for crystallization with ethanol. Other fatty acids can be synthesized and refined in the same manner as described above.

EXAMPLE 1

Figure 1:
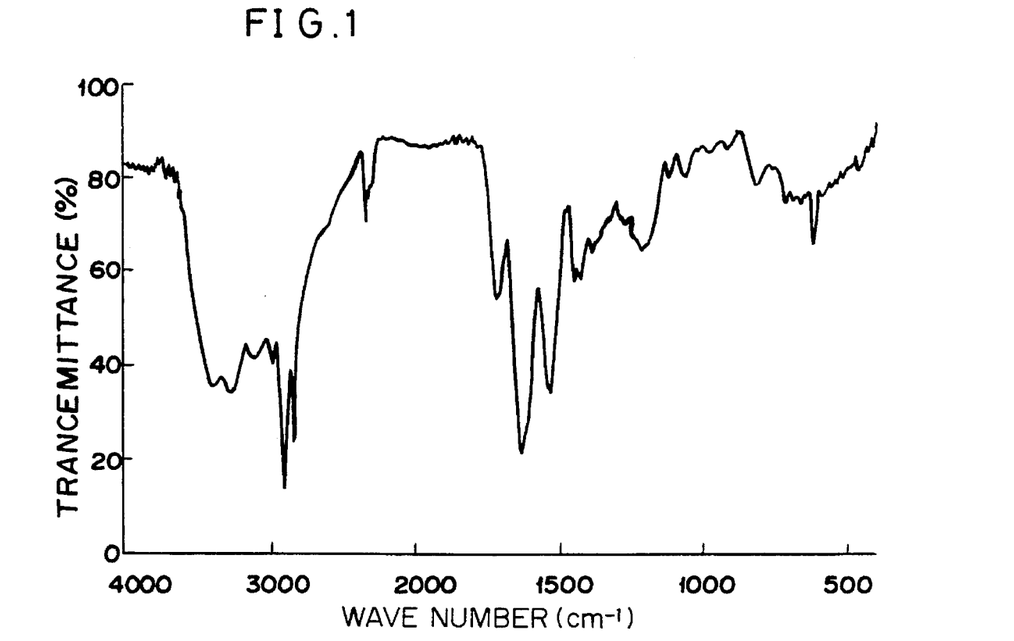
FIG. 1 is an infrared absorption spectrum of N-oleoyl carnosine, i.e. an N-acyl peptide according to this invention.

In 10 ml of water, 226 mg (1 m.mol) of carnosine and 84 mg (1 m.mol) of sodium hydrogen carbonate were dissolved. The resultant solution and a solution of 380 mg (1 m.mol) of the N-hydroxysuccinimide ester of oleic acid of high purity obtained in Reference Example in 10 ml of tetrahydroxyfuran added thereto were stirred at normal room temperature with a magnetic stirrer and thus left reacting with each other for 15 hours. From the resultant reaction solution, about 200 mg of N-oleoyl-carnosine of high purity was obtained by acidifying the reaction solution with 6N hydrochloric acid, extracting the acidified reaction product from ethyl acetate, and repeatedly subjecting the extract to a treatment for crystallization with hexane/ethyl acetate (4:1 v/v). This N-oleoyl-carnosine was analyzed by IR, , $^1$H-NMR and $^{13}$C-NMR. In the infrared spectrum, the absorption peaks, region of 2,920 $cm^{-1}$ and 2,830 $cm^{-1}$ (CH expansion), originating in oleic acid and the absorption peaks, 1,650 to 1,400 $cm^{-1}$ (C=C, C=N expansion), originating in imidazole were discernible. Further, a marked decrease was found in the peak, 1,4580 $cm^{-1}$ (NH deformation), prominent in the chart of carnosine. In the $^1$H-NMR spectrum, a chemical shift of the $C_9$, $C_{10}$ cis-form proton in the magnitude of 5.30 ppm originating in oleic acid was discernible. The integral ratio implied the presence of an amide bond between an oleic acid and a carnosine. From the —COOH of oleic acid, the magnitude of chemical shift of the proton of carbon at the alpha position was found to have shifted from 2.30 ppm to 2.00 ppm and that of chemical shift of the proton of carbon at the beta position was found to have shifted from 1.60 ppm to 1.45 ppm. In the $^{13}$C-NMR spectrum, the magnitude of chemical shift of the carbon of —COOH of oleic acid was found to have shifted from 180.40 ppm to 170.59 ppm. These results indicate that the oleic acid formed an amide bond with the beta-alanine residue of carnosine. The infrared absorption spectrum is shown in FIG. 1.

EXAMPLE 2

Figure 2:
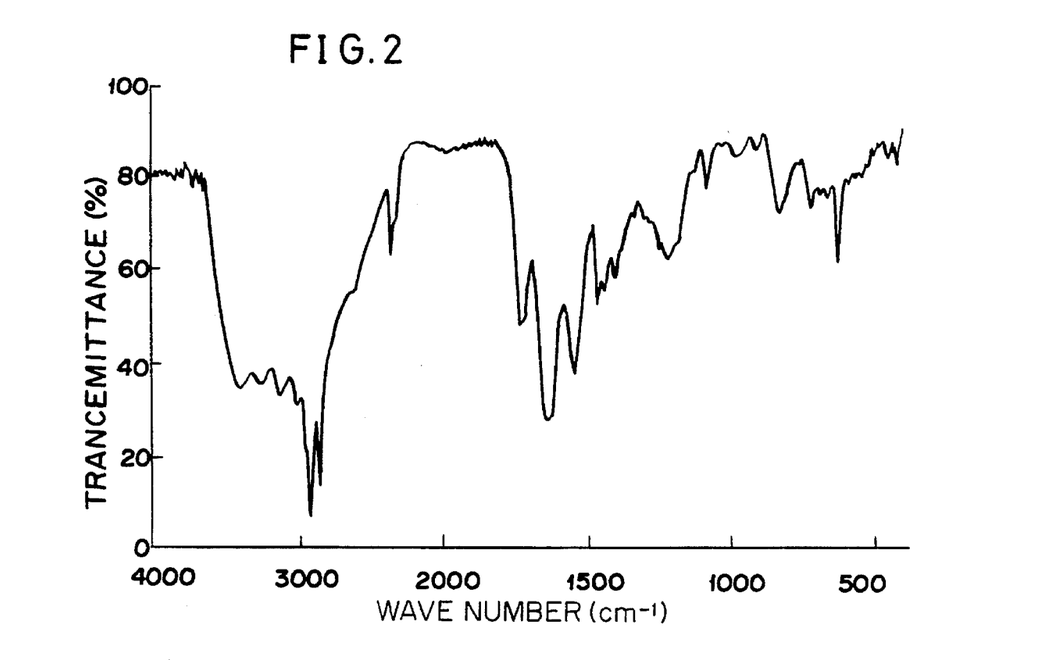
FIG. 2 is an infrared absorption spectrum of N-oleoyl histidine, i.e. an N-acylamino acid according to this invention.

About 150 mg of N-oleoyl-His of high purity was obtained by following the procedure of Example 1. This compound was analyzed by infrared absorption spectroscopy. In the spectrum, the absorption peaks, region of 2,920 $cm^{-1}$ and 2,850 $cm^{-1}$ (CH expansion), originating in oleic the absorption peaks, 1,650 to 1,400 $cm^{-1}$ (C=C, C=N expansion), originating in His were discernible. The structure of N-oleoyl-His was established by discernment of the absorption peaks, 3,400 to 3,100 $cm^{-1}$ (NH expansion), of amide. The infrared absorption spectrum of the N-oleoyl-His is shown in FIG. 2.

EXAMPLES 3-7

Figure 3:
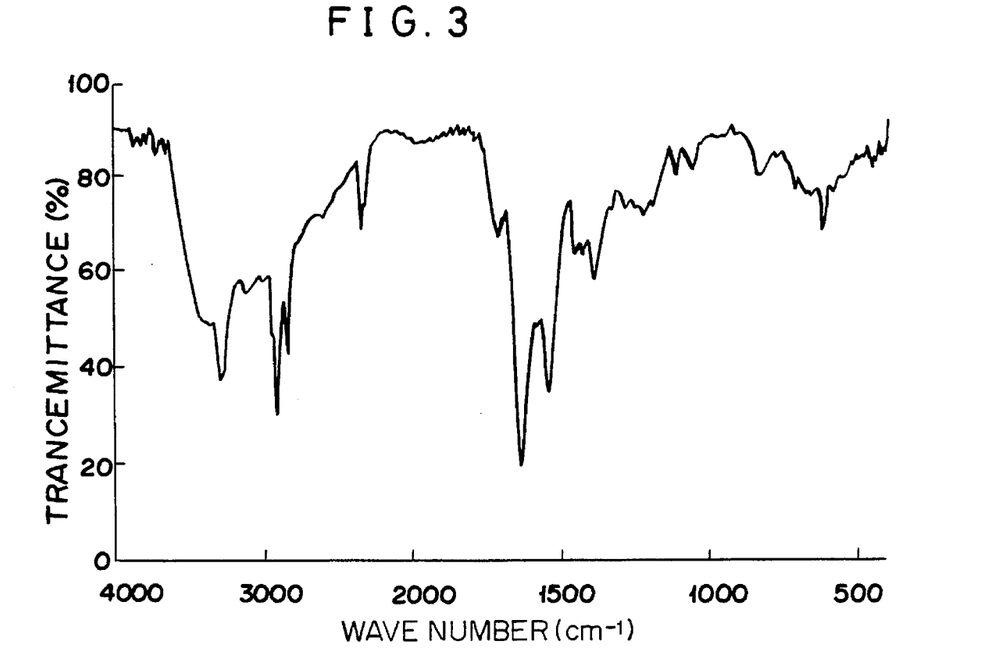
FIG. 3 is an infrared absorption spectrum of N-caprinoyl carnosine.
Figure 4:
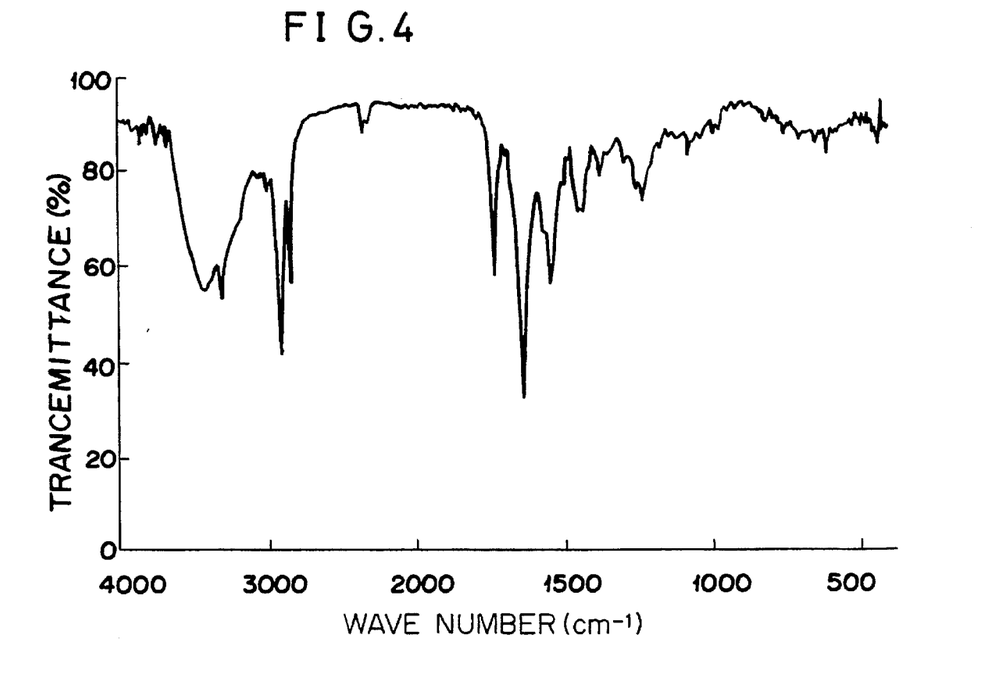
FIG. 4 is an infrared absorption spectrum of N-oleoyl carnosine methyl ester.
Figure 5:
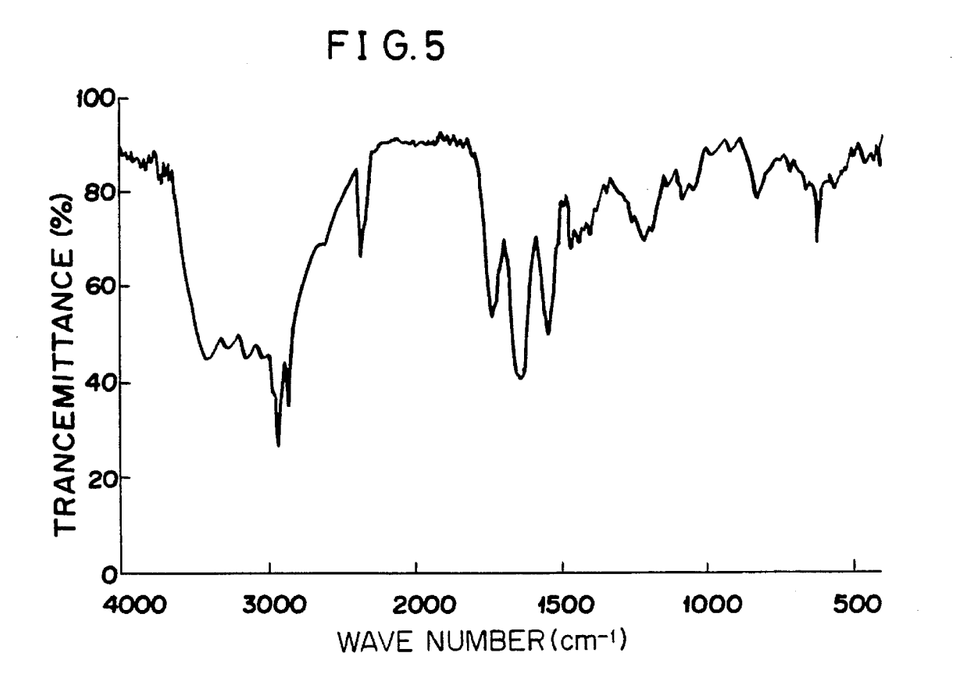
FIG. 5 is an infrared absorption spectrum of N-caprinoyl histidine.
Figure 6:
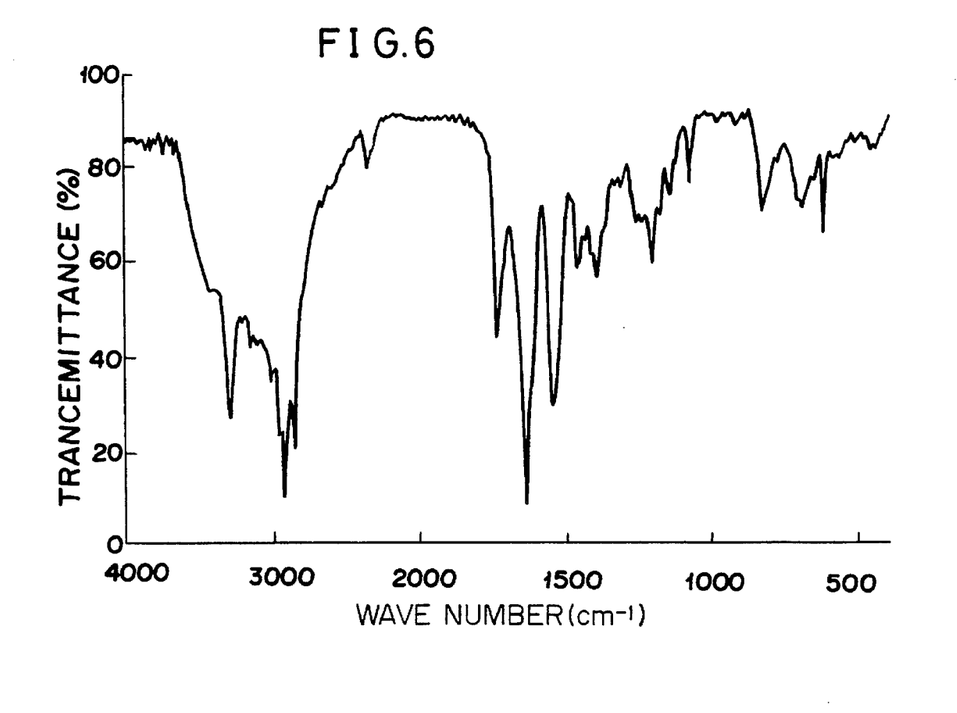
FIG. 6 is an infrared absorption spectrum of N-oleoyl histidylleucine.
Figure 7:
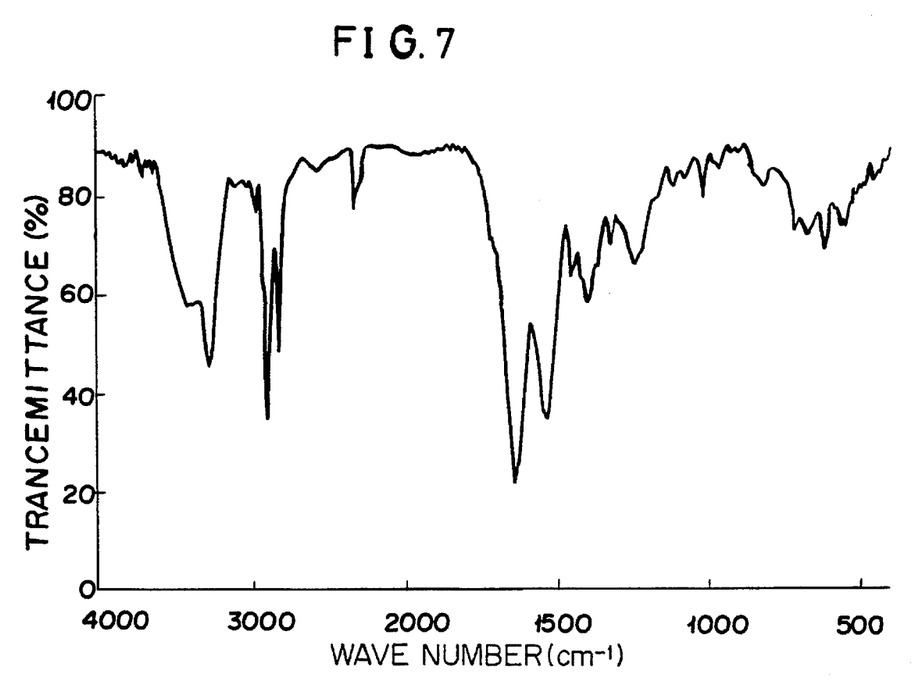
FIG. 7 is an infrared absorption spectrum of N-oleoyl glycylglycyl histidine.

N-Caprinoyl carnosine (Example 3), N-Oleoyl carnosine methyl ester (Example 4), N-caprinoyl histidine (Example 5), N-oleoyl histidylleucine (Example 6), and N-oleoyl glycylglycylhistidine (Example 7) were prepared by a similar method to Example 1. Infrared absorption spectra were shown FIG. 3 (Example 3), FIG. 4 (Example 4), FIG. 5 (Example 5), FIG. 6 (Example 6), and FIG. 7 (Example 7).

With other peptides, corresponding N-acyl-peptides can be easily synthesized and their structures analyzed in the same manner us described above.

EXAMPLES 8

Figure 8:
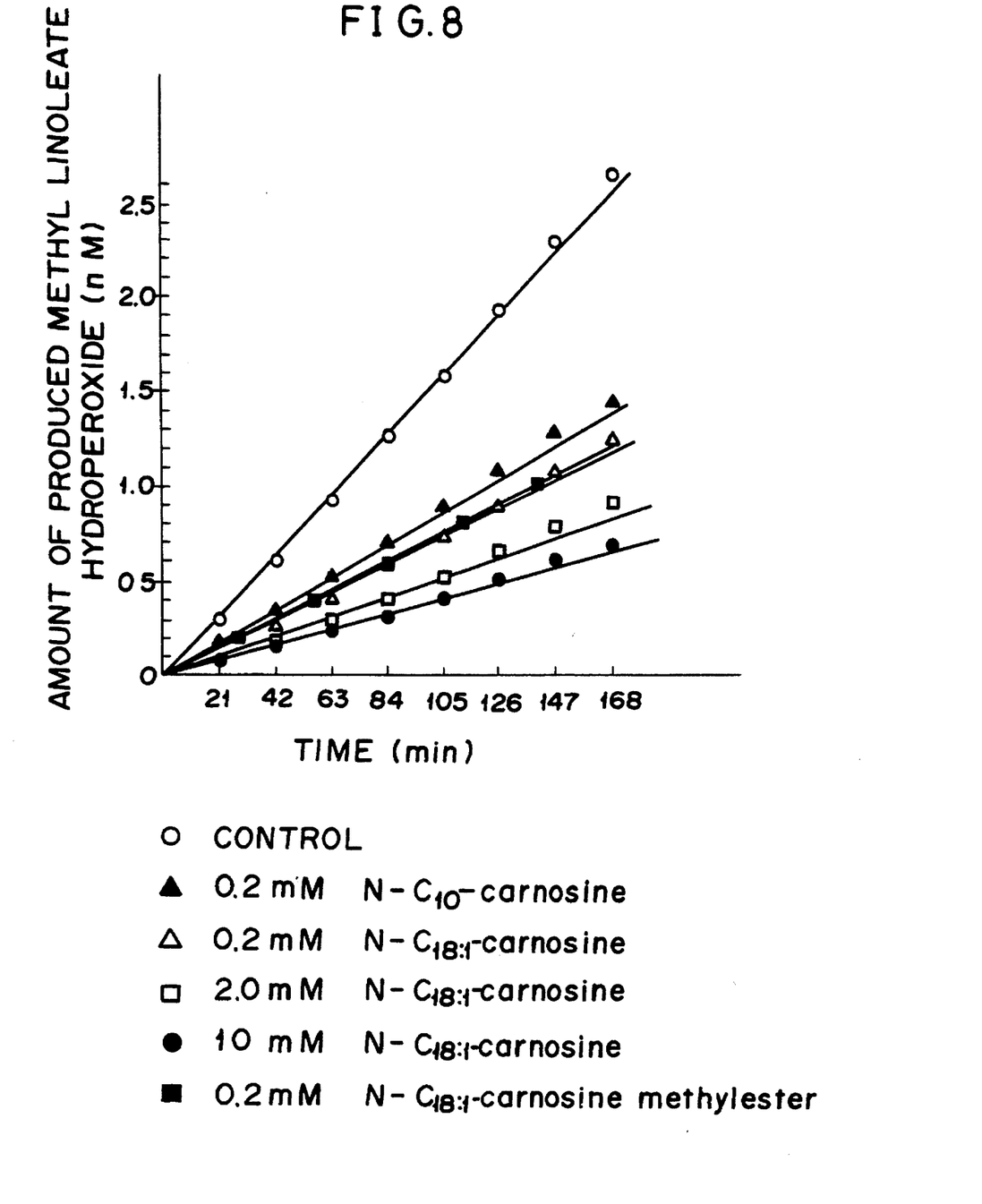
FIG. 8 is a graph showing the antioxidizing power of N-acylamino acid compounds according to this invention.

The N-oleoyl-carnosine, N-caprinoyl-carnosine and N-oleoyl-carnosine methyl ester obtained respectively in Examples 1, 3 and 4 were tested for antioxidizing power in terms of repression of the radical chain autoxidation reaction of methyl linoleate. Hexane/isopropyl alcohol (1:1 v/v) containing 100 mM of methyl linoleate, 10 mM of an oil-soluble generating agent (2,2'-azo-bis(2,4-dimethyl valeronitrile)), and various concentration of N-oleoyl-carnosine, N-caprinoyl-carnosine or N-oleoyl-carnosine methyl ester was kept incubated at 37° C., sampled at intervals along the course of time, and analyzed by high-performance liquid chromatography to follow changes in the amount of methyl linoleate hydroperoxide to be formed. The results of the test shown in FIG. 8 clearly indicate that both of the compounds were possessed of antioxidizing power.

EXAMPLE 9

Figure 9:
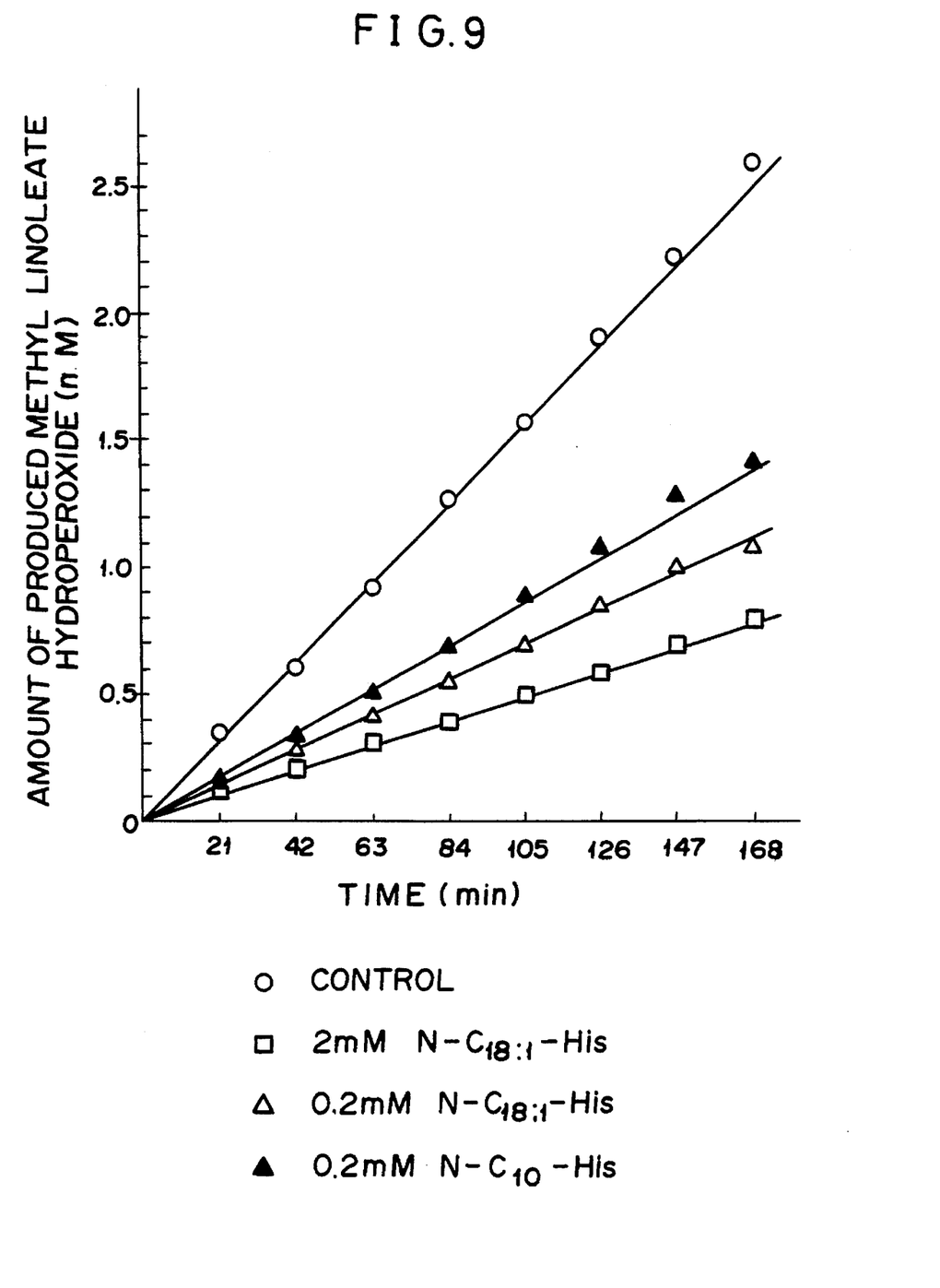
FIG. 9 is graph showing the antioxidizing power of N-acylamino acid compounds according to this invention.

Antioxidizing powers of N-oleoyl histidine and N-caprinoyl histidine obtained respectively in Examples 2 and 5 were determined by a similar method to Example 8 to find that they have antioxidizing powers as shown in FIG. 9.

EXAMPLE 10

Figure 10:
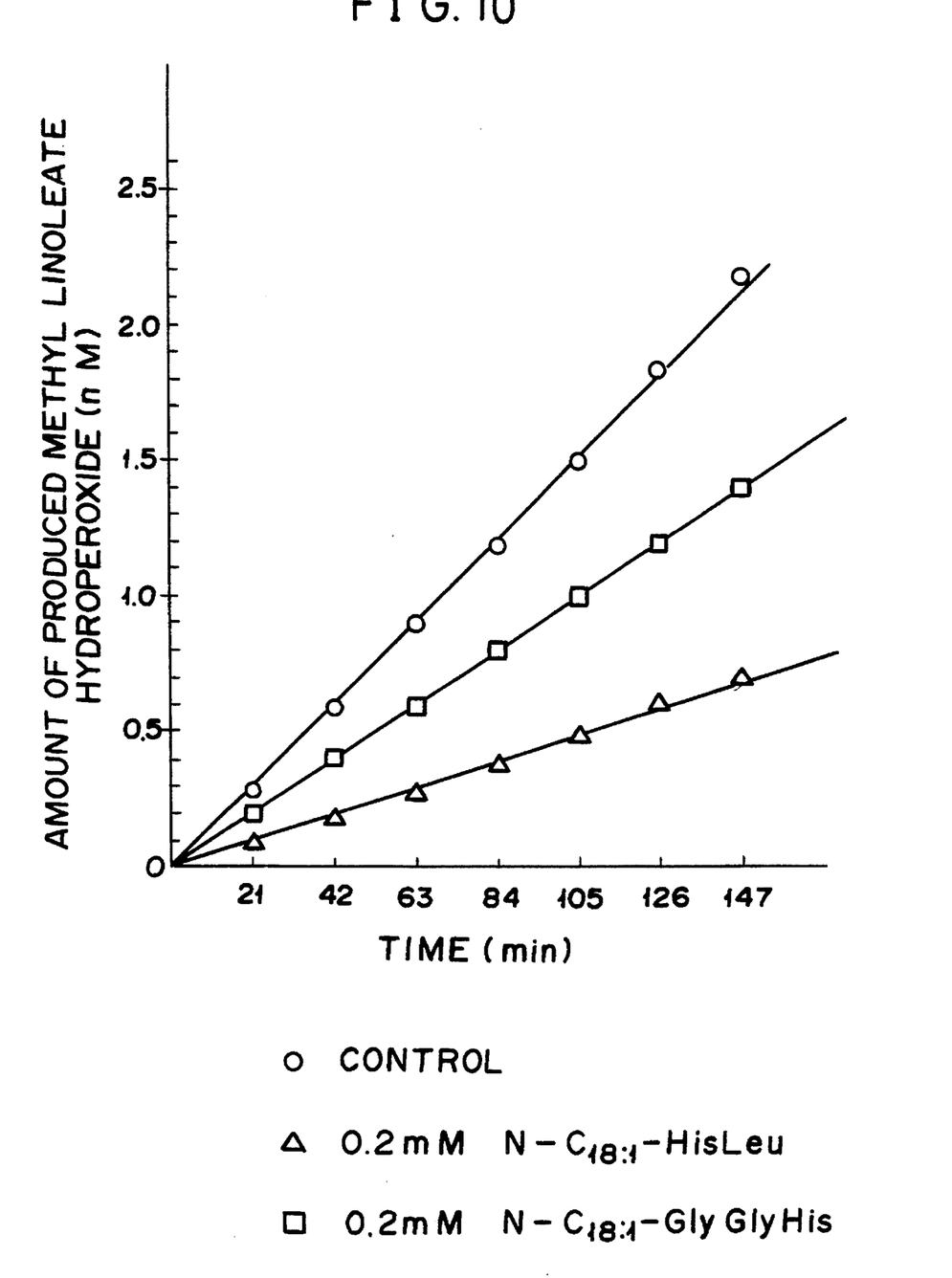
FIG. 10 is a graph showing the antioxidizing power of N-acylamino acid compounds according to this invention.

Antioxidizing powers of N-oleoyl histidylleucine and N-oleoyl glycylglycylhistidine obtained respectively in Examples 6 and 7 were determined by a similar method to Example 8 to find that they have antioxidizing powers as shown in FIG. 10.

EXAMPLE 11

Figure 11:
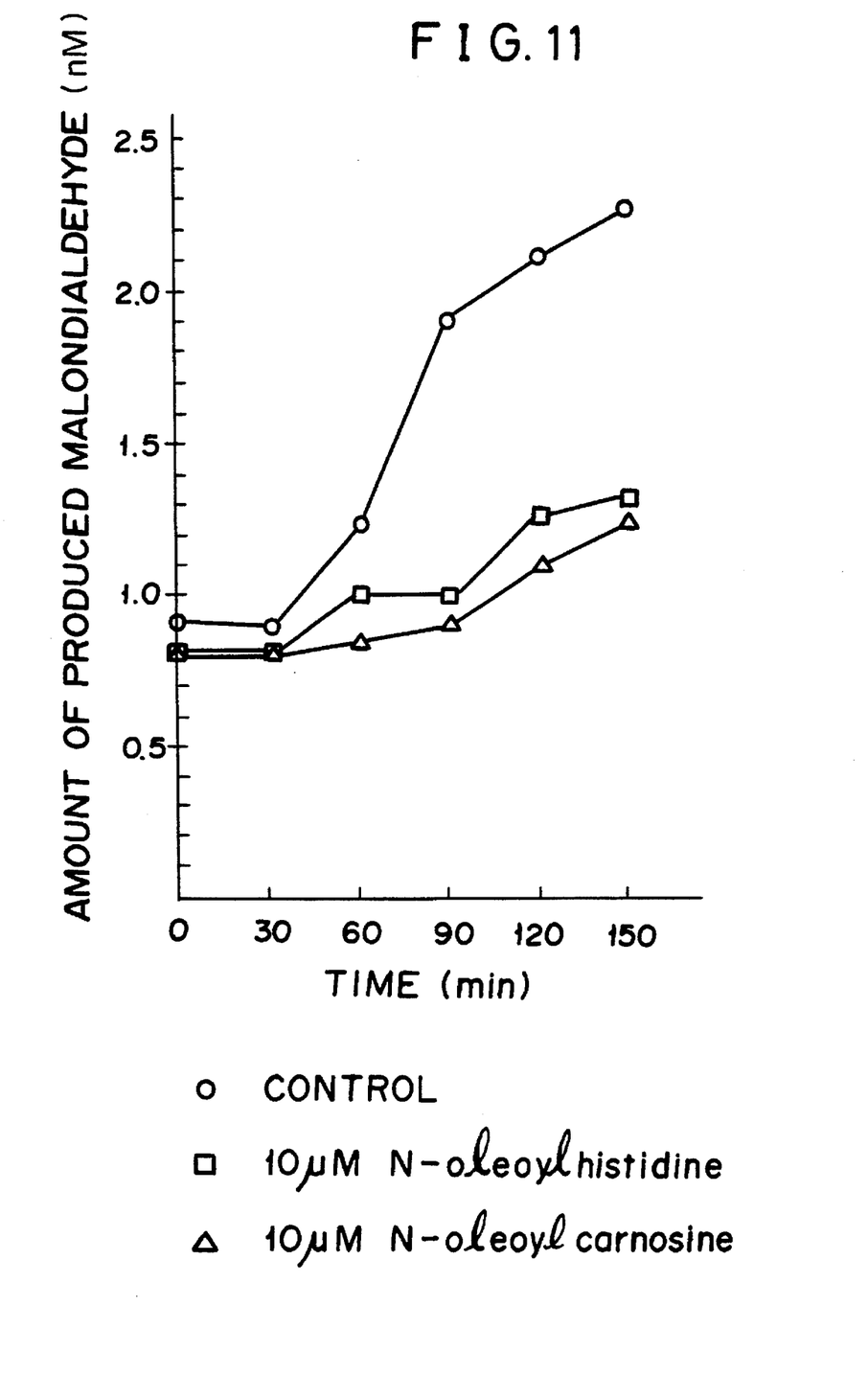
FIG. 11 is a graph showing the antioxidizing power of N-acylamino acid compounds according to this invention.

The N-oleoyl-carnosine and the N-oleoyl-histidine obtained respectively in Example 1 and Example 2 were tested for antioxidizing power in terms of the repression of the radical chain autoxidizing reaction of a multilayer liposome. A multilayer liposome was formed of 4 mM of egg yolk phosphatidylcholine, 0.4 mM of egg yolk phosphatidylcholine hydroperoxide, and 10 μM of N-oleoylcarnosine or N-oleoyl-histidine by the use of 10 mM trishydrochloric acid buffer solution (pH 7.4). The multilayer liposome and 0.1 mM of ferrous sulfate and 1 mM of ascorbic acid added thereto were incubated at 37° C., sampled at intervals along the course of time, subjected to the TBA reaction to induce coloration of malondialdehyde resulting from the hydrolysis of lipid peroxide, and analyzed by high-performance liquid chromatography to follow changes in the amount of the hydrolyzate. The results of test shown in FIG. 11 indicate that the compounds were possessed of antioxidizing power and chelating power.

EXAMPLE 12

The N-oleoyl-carnosine and the N-oleoyl-histidine obtained respectively in Example 1 and Example 2 were tested for emulsifying power. The emulsifying power was determined by dissolving each N-acyl compound in a concentration of 0.2% in 50 mM of phosphate buffer solution (pH 7), combining the resultant solution with one half in volume of soybean oil, subjecting the resultant mixture to a treatment with ultrasonic wave at 30° C., allowing the treated mixture to stand at rest at 30° C. for a prescribed time, and measuring the turbidity of the lower layer consequently separated in the mixture in terms of O.D. (500 nm). The results of test shown in Table 1 indicate that N-oleoyl-carnosine and N-oleoyl-histidine were possessed of outstanding emulsifying power. The magnitudes of emulsifying power given in Table 1 represent relative numerical values of emulsifying power based on the emulsifying power of N-oleoyl-carnosine taken as 100.

TABLE 1

| Emulsifier | Relative emulsifying activity (%) |
|---|---|
| Tween 80 | 46.5 |
| Casein | 24.3 |
| Sugar ester | 19.4 |
| Triton X100 | 9.7 |
| N-oleoyl-His | 82.1 |
| N-oleoyl-carnosine | 100 |

What is claimed is:

1. An antioxidant having as an active component thereof an N-acylcarnosine compound represented by the formula (1):

$$R-CO-(NH-X-CO)_n-OR^1 \qquad (1)$$

wherein (NH—X—CO) is a carnosine radical, R—CO is a saturated or unsaturated fatty acid radical having 6 to 24 carbon atoms, inclusive, $R^1$ is a hydrogen atom, a sodium atom, a potassium atom, or a methyl group, and n is 1 or 2.

2. An antioxidant of claim 1 wherein the R—CO is a saturated or an unsaturated fatty acid radical having 8 to 20 carbon atoms.

3. An antioxidant of claim 1 wherein the N-acylcarnosine compound is N-oleoyl carnosine.

4. An antioxidant of claim 1 wherein the N-acylcarnosine compound is selected from the group consisting of N-caprinoyl carnosine, N-oleoyl carnosine methyl ester, and N-oleoyl carnosine.

5. A method of protecting a substrate against oxidation which comprises the step of applying to the substrate to be protected an antioxidant having as an active component thereof an N-acylcarnosine compound represented by the formula (1):

$$R-CO-(NH-X-CO)_n-OR^1 \qquad (1)$$

wherein (NH—X—CO) is a carnosine radical, R—CO is a saturated or unsaturated fatty acid radical having 6 to 24 carbon atoms, inclusive, $R^1$ is a hydrogen atom, a sodium atom, a potassium atom, or a methyl group, and n is 1 or 2.

6. A method of claim 5 wherein the R—CO is a saturated or an unsaturated fatty acid radical having 8 to 20 carbon atoms.

7. A method of claim 5 wherein the N-acylcarnosine compound is N-oleoyl carnosine.

8. A method of claim 5 wherein the N-acylcarnosine compound is selected from the group consisting of N-caprinoyl carnosine, N-oleoyl carnosine methyl ester, and N-oleoyl carnosine.

\* \* \* \* \*

UNITED STATES PATENT AND TRADEMARK OFFICE
CERTIFICATE OF CORRECTION

PATENT NO. : 5,503,776
DATED : April 2, 1996
INVENTOR(S) : Hironobu Murase, Tsutomu Kunieda, Akihiko Nagao, Junji Terao It is certified that error appears in the above-indentified patent and that said Letters Patent is hereby corrected as shown below:

Column 6, line 17: "originating in oleic" should read -- originating in oleic acid and --.

Signed and Sealed this

Thirtieth Day of July, 1996

Attest:

BRUCE LEHMAN

Attesting Officer    Commissioner of Patents and Trademarks